United States Patent [19]

Miwa et al.

[11] Patent Number: 4,675,337

[45] Date of Patent: Jun. 23, 1987

[54] NON-MUTAGENIC 1,2-DISUBSTITUTED 4-NITRO-IMIDAZOLES USEFUL AS ANTIPROTOZOAL AGENTS

[75] Inventors: Gerald T. Miwa, Maplewood; Wen-Jen R. Wang, Montvale; John S. Walsh, Garwood, all of N.J.

[73] Assignee: Merck & Co., Inc., Rahway, N.J.

[21] Appl. No.: 835,026

[22] Filed: Feb. 28, 1986

[51] Int. Cl.$^4$ .................. A61K 31/415; C07D 233/91
[52] U.S. Cl. ..................................... 514/398; 548/338
[58] Field of Search ......................... 548/338; 514/398

[56] References Cited

U.S. PATENT DOCUMENTS 3,644,392  2/1972  Henry ................................. 548/338

OTHER PUBLICATIONS

*Indian Journal of Chemistry*, Section B, 21B(11), pp. 1006–1021 (1982).

*Primary Examiner*—John M. Ford
*Assistant Examiner*—Robert C. Whittenbaugh
*Attorney, Agent, or Firm*—David L. Rose; Manfred Polk; Michael C. Sudol, Jr.

[57] ABSTRACT

The invention relates to novel 1,2-disubstituted-4-nitroimidazole compounds that are useful as potent antiprotozoal agents and simultaneously possess non-mutagenicity as compared to known 4- or 5-nitroimidazole compounds. Also, compositions and methods for antiprotozoal uses of said novel 1,2-disubstituted-4-nitroimidazole compounds are disclosed herein.

16 Claims, No Drawings

NON-MUTAGENIC 1,2-DISUBSTITUTED 4-NITRO-IMIDAZOLES USEFUL AS ANTIPROTOZOAL AGENTS

BACKGROUND OF THE INVENTION

The invention relates to novel 1,2-disubstituted-4-nitroimidazole compounds being useful as potent antiprotozoal agents which possess non-mutagenic activity. The novel compounds disclosed herein are useful in formulating compositions comprising an effective amount of said novel compounds and methods of administering said compositions.

Nitroimidazoles are a class of known compounds and have the reputation as mutagens. Metronidazole (flagyl), a 5-nitro-imidazole is mutagenic and consequently raises concern over safety when administered to patients. Also, the compound, 1-methyl-2-methylsulfonyl-4-nitroimidazole is a known compound and is disclosed in the Indian Journal of Chemistry, Section B, 21B (11), pp. 1006-21. The utility of this compound was disclosed as being active as radio and chemosensitizers and no mention was made of any biological activities or relative mutagenicity. The novel compounds disclosed in the invention herein are not mutagenic in Ames strain TA100, and are highly potent against protozoal diseases and, therefore, offer a greater safety advantage to patients. Said novel compounds are of particular use against Trichomonas spp. such as *T. foetus* and *T. vaginalis*.

SUMMARY OF THE INVENTION

The invention relates to novel non-mutagenic 1,2-disubstituted-4-nitroimidazole compounds that are useful as potent antiprotozoal agents.

Accordingly, it is an object of the invention to provide a class of novel 1,2-disubstituted-4-nitroimidazole compounds.

A further object of the invention is to describe processes for the preparation of said novel nitroimidazole compounds.

Another object of the invention is to provide pharmaceutical compositions for administering an effective amount of said novel compounds to patients (warm blooded animals).

These and other objects and advantages of the invention will become apparent from the following description.

DESCRIPTION OF THE INVENTION

The invention relates to novel non-mutagenic 1,2-disubstituted-4-nitroimidazole compounds that are potent antiprotozoal agents. Said novel 4-nitroimidazole compounds of the invention have the following general structure:

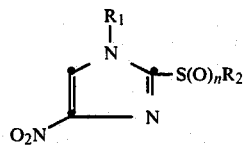

wherein:
R$_1$ is alkyl(C$_1$–C$_6$) such as methyl, ethyl, isopropyl, pentyl and the like; or arylalkyl(C$_7$–C$_9$), preferably phenylalkyl(C$_1$–C$_3$) such as benzyl, phenylethyl and the like;
R$_2$ is alkyl(C$_1$–C$_{12}$) such as methyl, ethyl, isopropyl, heptyl, decyl and the like; or phenyl; and
n is 0, 1 or 2;
with the proviso that when n is 2, R$_1$ or R$_2$ is other than methyl.

The preferred compounds of the invention are:
1-methyl-2-ethylsulfonyl-4-nitroimidazole;
1-methyl-2-propylsulfonyl-4-nitroimidazole;
1-methyl-2-isopropylsulfonyl-4-nitroimidazole;
1-methyl-2-phenylsulfonyl-4-nitroimidazole;
1-methyl-2-methylsulfinyl-4-nitroimidazole;
1-methyl-2-methylthio-4-nitroimidazole;
1-methyl-2-ethylthio-4-nitroimidazole;
1-methyl-2-propylthio-4-nitroimidazole;
1-methyl-2-isopropylthio-4-nitroimidazole;
1-methyl-2-ethylsulfinyl-4-nitromidazole.

The novel compounds disclosed herein are prepared by processes known in the art. Generally, said compounds are prepared by treating 1-alkyl or arylalkyl-2-mercaptoimidazole with a base in the presence of an alcohol solvent and an alkylhalide at room temperature and then with nitric acid and water. The reaction is heated to 100° C. for about 1.0 to 1.5 hours to obtain the corresponding 1-alkyl or arylalkyl-2-alkylthio-5-nitroimidazole. This product is then dissolved in an acid (weak), treated with hydrogen peroxide and heated to 100° C. for approximately an hour. The resulting 1-alkyl or 1-arylalkyl-2-alkylsulfonyl-5-nitroimidazole is dissolved in an inert solvent and potassium iodide added therein and heated gently to reflux to obtain the corresponding 1-alkyl or arylalkyl-2-alkylsulfonyl-4-nitroimidazole.

Treating 1-alkyl or arylalkyl-2-alkyl or arylalkylthio-4-nitroimidazole with an organic peracid (m-chloroperbenzoic acid) in the presence of an inert solvent at room temperature for approximately 1.5 to 3.0 hours gives the corresponding 1-alkyl or arylalkyl-2-arylalkylsulfinyl or alkylsulfinyl-4-nitroimidazole.

Refluxing 1-alkyl-2-methylsulfonyl-4-nitroimidazole with alkyl or arylalkylmercaptans in strongly basic solvent for approximately 2 hours gives the corresponding 1-alkyl or arylalkyl-2-alkylthio or arylalkylthio-4-nitroimidazole.

Nitroimidazoles are known generally to be mutagenic compounds and are usable only in those instances where the disease being treated is of such a level of seriousness that the negative effects of the mutagenicity of the compound are balanced against the conditions resulting from the disease. Thus, the discovery of a non-mutagenic drug which could be used to treat protozoal diseases has been long sought.

One very well accepted measure of the mutagenicity of chemicals, which has generally also been closely correlated with the carcinogenicity of such compounds, is the Ames Mutagenicity Test. This test involves the addition to a fermentation medium in which is growing a particular organism identified as Ames Salmonella TA100, and measuring the number of mutant organisms formed. Greater numbers of mutants over the background number of spontaneous mutants is an indication of greater mutagenicity of the compound. Generally a series of varying concentrations of the test compound is employed to determine threshold levels if possible.

In one such Ames mutagenicity test 1-methyl-2-ethylthio-4-nitroimidazole was compared to two commercially available nitroimidazoles, ronidazole(1-methyl-2-[(carbamoyloxy)methyl]-5-nitroimidazole) and metronidazole(1-(2-hydroxyethyl-2-methyl-5-nitroimidazole). At 3 μg per plate ronidazole had 358 mutants per plate while metronidazole and the instant compound were indistinguishable from background. At 30 μg per plate, ronidazole had 2682 mutants per plate and metronidazole had 142 mutants per plate while the instant compound was still indistinguishable from background. At 100 and 300 μg per plate metronidazole had 443 and 1374 mutants per plate respectively, while the instant compound was still at barely a threshold level of 30 and 65 mutants per plate respectively. The instant compound continued to show no significant levels at 30, 100, 300 and 1000 μg per plate by recording 0, 54 and 0 mutants per plate respectively. Such levels of mutagenicity are not statistically significantly different from background and as such, the instant compound would be considered non-mutagenic.

Thus, considering the rapidly increasing mutagenic activity of ronidazole and metronidazole and the continuing statistically insignificant levels of mutagenic activity with the instant compound, it is apparent that the instant compound represents a considerable breakthrough in treating protozoal diseases with a new level of safety, unachieved and unachievable with prior therapies.

The instant compounds have antiprotozoal activity, and is particularly active against the causative organisms of the protozoal parasitic diseases trichomoniasis and enterohepatitis. It is also effective against amoebiasis and trypanosomiasis, as well as against the PPLO organisms and schistosomes.

Trichomoniasis is a protozoan disease caused by parasites of the genus Trichomonas. The compound of the invention is effective against the particularly troublesome form of trichomoniasis known as *T. vaginalis* vaginitis, caused by infestation of the vagina with *T. vaginalis*. In treating this disease, the compound may be administered either orally or topically. For oral administration unit dosage, forms such as tablets or capsules are normally employed which may contain from about 25 to about 1000 mg of active ingredient. These are prepared by techniques known in the art, and contain the usual diluents, granulating agents, extenders and/or lubricating agents known to be satisfactory for the compounding of tablets and capsules. It is preferred to administer the compound of the invention orally at a dose level of from about 50–500 mg/day, in either single or divided doses with divided doses being used more frequently than a single dose. An example of a suitable compressed tablet contains the ingredients below:

|  | Mg per tablet |
| --- | --- |
| 1-methyl-2-ethylthio-4-nitroimidazole | 250 |
| Dicalcium phosphate | 100 |
| Lactose | 75 |
| Starch | 50 |
| Guar gum | 12 |
| Magnesium stearate | 2–3 |

If desired, tablets may be sugar coated or enteric coated by standard techniques. Alternatively, the antitrichomonal agent may be formulated in capsule form using fillers such as lactose, starch or kaolin. A typical capsule would contain 250 mg of, for instance, 1-methyl-2-ethylthio-4-nitroimidazole, 2–3 mg of magnesium stearate and about 75 mg of lactose in a No. 0 size capsule. Tablets and capsules containing smaller quantities of active ingredient may be made by reducing proportionately the amounts of excipients and diluents illustrated above. Alternatively, the compound may be administered orally in liquid pharmaceutical vehicles such as solutions, emulsions, syrups or suspensions containing the diluents, flavoring agents and preservatives customarily employed in the pharmaceutical art.

For topical application such as creams or ointments and suppositories these formulations may be prepared via conventional methods containing the active ingredient. To illustrate, a cream or ointment or suppository is prepared by mixing sufficient quantities of hydrophilic material and water, containing from about 5–10% by weight of the compound, in sufficient quantities to produce a cream or ointment or suppository having the desired consistency.

Enterohepatitis is a disease occurring primarily in turkeys and is caused by the protozoan parasite *Histomonas meleagridis*. It is also known as turkey blackhead disease. The compound of this invention is useful in the prevention and treatment of this disease and for this purpose is administered to turkeys mixed with an element of turkey sustenance, i.e. in the feed or drinking water. Although the optimum dose level will depend on the severity of the infection, good control of enterohepatitis is obtained by orally administering to the turkeys a feed containing from about 0.003% to about 0.1% by weight of the instant compound. When the material is administered via the drinking water, somewhat higher levels may be employed, especially for therapeutic use. For instance, the drinking water may contain up to about 0.2% by weight of the active ingredient with good results.

As previously stated, the compound described herein may also be employed against trypanosomiasis, amoebiasis and the pleuro-pneumonia like organisms which have come to be known as PPLO.

The compound is effective against PPLO when the compound is administered to fowl or swine in feed containing from about 0.003% to about 1.0% by weight of carbamate. The preferred dosage level, however, is between from about 0.003% to 0.08% by weight.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Some studies which further exemplify the invention are listed below:

Mice were infected through intraperitoneal (I.P.) injection of $1.4 \times 10^7$ *T. foetus*. Each compound disclosed in Table I below was dissolved in an aqueous vehicle, dosed to groups of mice (consisting of five) by gavage. The mice were dosed once per day for four consecutive days with doses ranging from 1–50 mg/kg. The effective dose of the compound, $ED_{50}$, was calculated from the number of animals surviving a two week period.

TABLE I

Trichomonal Activity of 1-($R_1$)-2-($R_2$)-4-Nitroimidazoles and Flagyl

| Compound | $R_1$ | $R_2$ | $ED_{50}$ (T. foetus) in vitro (μg/ml) | in vivo (mg/kg) |
|---|---|---|---|---|
| 1. | —$CH_2CH_3$ | —$SO_2CH_3$ | 25 | 10–50 |
| 2. | —$CH_3$ | —$SO_2CH_2CH_3$ | 18.5 | 2–5 |
| 3. | —$CH_3$ | —$SO_2CH_2CH_2CH_3$ | 27 | 5–10 |
| 4. | —$CH_3$ | —$SO_2$—iPr | 21 | 5–10 |
| 5. | —$CH_3$ | —$SO_2Ph$ | 17 | 10–25 |
| 6. | —$CH_3$ | —$SOCH_3$ | 14 | 2–5 |
| 7. | —$CH_3$ | —$SCH_3$ | 2.1 | 5–10 |
| 8. | —$CH_3$ | —$SCH_2CH_3$ | 2.3 | 2 |
| 9. | —$CH_3$ | —$SCH_2CH_2CH_3$ | 4.0 | 5 |
| 10. | —$CH_3$ | —S—iPr | 4.0 | 10–50 |
| 11. | FLAGYL | | 0.4 | 25–50 |

As indicated in Table I above, the novel compounds of the invention as compared to Flagyl (a commonly used nitroimidazole) are from 1.5 to 25 times more active.

TABLE II

Mutagenicity and Trichomonal Activities of 4-Nitroimidazoles Relative to 5-Nitroimidazoles

| Compound | Mutagenicity (percent Ronidazole) | T. foetus ($ED_{50}$) In vivo (mg/kg) | In Vivo* Safety Index (rel to flagyl) |
|---|---|---|---|
| 1-methyl-2-ethylthio-4-nitroimidazole | <0.1** | 2 | >1750 |
| 1-methyl-2-methanol carbamate (ester)-5-nitroimidazole (Ronidazole) | 100 | 2–5 | 0.7 |
| 1-(2-hydroxyethyl)-2-methyl-5-nitroimidazole (Flagyl) | 7 | 50 | 1.0 |

*In vivo Safety Index is the relative increase in safety (1/mutagenicity) observed at the $ED_{50}$ dose. All values are expressed relative to flagyl. The larger the number the greater the relative safety compared to flagyl. Therefore, the representative compounds of this invention are greater than 1750 times safer than flagyl at the therapeutic dose.

**Mutagenicity was undetectable. (Less than 0.1% of the mutagenicity of ronidazole).

TABLE III

Mutagenic Activity of 4-Nitroimidazoles in Ames TA100 Strain

| R1 | R2 | Mutagenicity* (percent ronidazole) | T. foetus ($ED_{50}$) In vivo (mg/kg) |
|---|---|---|---|
| —$CH_3$ | —$SO_2CH_2CH_3$ | 0.1 | 2–5 |
| —$CH_3$ | —$SO_2CH_2CH_2CH_3$ | 0.1 | 5–10 |
| —$CH_3$ | —$SO_2$—i-Pr | 0.1 | 5–10 |
| —$CH_3$ | —$SO_2Ph$ | 0.1 | 10–25 |
| Flagyl | | 7.0 | 25–50 |
| Ronidazole | | 100.0 | 5–10 |

*Mutagenicity values of all novel compounds disclosed herein are undetectable (<0.1% relative to the mutagenicity of ronidazole).

TABLE IV

Single Strand DNA Breaks and Cytotoxicity In Rat Hepatocytes

| Treatment | Concentration | Relative* Elution Slope | Relative** Viability (%) |
|---|---|---|---|
| Control | — | 1.00 | 100 |
| Flagyl | 3.0 mM | 5.33 | 107 |
| | 10.0 mM | 7.1 | 101 |
| 1-methyl-2-ethylthio-4-nitroimidazole | 0.5 mM | 1.33 | 107 |
| | 1.5 mM | 1.23 | 105 |
| | 5.0 mM | 1.60 | 102 |

*Measure of the extent of DNA strand cleavage. Only relative elution slopes ≥3.0 are considered significant. Therefore, 1-methyl-2-ethylthio-4-nitroimidazole did not cause significant DNA strand breakage up to 5.0 mM while Flagyl caused breaks at both 3.0 and 10.0 mM.

**Relative viability is the number of hepatocytes surviving exposure to the nitroimidazoles relative to the control cells.

The following examples illustrate preparation of various novel 1,2-disubstituted-4-nitroimidazole compounds of the invention. Said examples should be construed as illustrations rather than limitations thereof.

EXAMPLE 1

1-Methyl-2-ethylthio-4-nitroimidazole

Ethyl mercaptan (5.14 g, 0.083 mole) was added to dimethylformamide (140 ml) containing potassium hydroxide (4.6 g, 0.08 mole). This was stirred for 90 minutes until all the potassium hydroxide had dissolved. To this solution was added 1-methyl-2-methylsulfonyl-4-nitroimidazole (8.5 g, 0.04 mole) and the reaction stirred for 2 hours at room temperature. The reaction mixture was then added to water (500 ml) and stirred in an ice bath for an additional hour. The crystalline product was filtered off and dried to give 5.6 g of crude product. This was recrystallized from ethanol/water to give 4.3 g of product.

EXAMPLE 2

1-Methyl-2-ethylsulfonyl-4-nitroimidazole

1-Methyl-2-mercaptoimidazole (5 g, 0.044 mole) was dissolved in methanol (150 ml) and 50% sodium hydroxide solution was added (3.5 ml, 0.044 mole). Ethyl iodide (7.0 ml, 0.087 mole) was then added and the reaction stirred at room temperature for 90 minutes. The reaction mixture was concentrated to 50 ml on a rotovap and then diluted with water (130 ml). This was extracted into three volumes of ether which was dried over sodium sulfate and then evaporated to give a clear oil. The oil was treated with a solution of concentrated nitric acid and water (20 ml of 70% nitric acid and 8 ml of water) and heated at 100° C. for 75 minutes. After cooling to room temperature, the reaction mixture was added to 200 ml of water and made basic with concentrated ammonium hydroxide solution. This was cooled in an ice bath where upon the 5-nitroimidazole product crystallized (2.3 g). The crystalline material (2.0 g, 0.011 mole) was dissolved in glacial acetic acid (15 ml) and treated with 30% hydrogen peroxide solution (3.1 ml, 0.027 mole). The reaction mixture was heated at 100° C. for 60 minutes. After cooling to room temperature, the reaction mixture was added to water (150 ml) and adjusted to pH 7 with concentrated ammonium hydroxide solution. This was then extracted with ether (3×100 ml), the ether layers combined, dried over sodium sulfate and evaporated to give 2.06 g of sulfone. The sulfone (1.9 g, 8.7 mmole) was dissolved in dimethylformamide (20 ml) and potassium iodide (1.59 g, 9.6 mole) was added. The reaction mixture was heated gently at reflux for 60 minutes. After cooling to room temperature, the reaction mixture was added to water (125 ml) with stirring. The flask was cooled in ice and the crystalline product filtered off to give 1.46 g of 4-nitroimidazole product.

EXAMPLE 3

1-Methyl-2-ethylsulfinyl-4-nitroimidazole

1-Methyl-2-ethylthio-4-nitroimidazole (200 mg, 1.07 mmole) was stirred in methylene chloride (5 ml). A solution of m-chloroperbenzoic acid (250 mg, 1.45 mmole) in methylene chloride (5 ml) was added dropwise over 40 minutes. The reaction was stirred at room temperature for a further 2 hours and then diluted with methyl chloride and washed successively with solutions of sodium sulfite, sodium carbonate, and water. The organic layer was dried over sodium sulfate and evaporated to give an oil. This was purified on a silica gel column eluted with 1% methanol in methylene chloride and 2% methanol in methylene chloride to give 100 mg of product.

What is claimed is:

1. A compound of the formula:

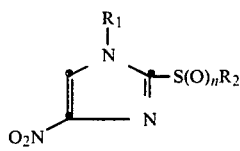

wherein $R_1$ is alkyl($C_1$–$C_6$) or phenyl substituted alkyl($C_7$–$C_9$);

$R_2$ is alkyl($C_1$–$C_{12}$) or phenyl; and n is 0, 1 or 2;

with the proviso that when n is 2, $R_1$ and $R_2$ are other than alkyl.

2. The compound of claim 1 wherein $R_1$ is alkyl, $R_2$ is alkyl and n is 0 or 1.

3. The compound of claim 1, wherein said $R_1$ alkyl is selected from the group consisting of methyl and propyl; and said $R_2$ alkyl is selected from the group consisting of methyl, ethyl, propyl, octyl and decyl.

4. The compound of claim 3, wherein $R_1$ is methyl, $R_2$ is ethyl and n is 0.

5. The compound of claim 3, wherein $R_1$ is methyl, $R_2$ is propyl and n is 0.

6. The compound of claim 3, wherein said $R_1$ alkyl is methyl; said $R_2$ alkyl is ethyl and n is 1.

7. The compound of claim 3, wherein said $R_1$ alkyl is methyl; said $R_2$ alkyl is propyl or isopropyl and n is 1.

8. The compound of claim 3, wherein said $R_1$ alkyl is methyl; said $R_2$ alkyl is methyl and n is 1.

9. A composition for non-mutagenic treatment of protozoal diseases which comprises a therapeutically effective amount of a compound of the formula:

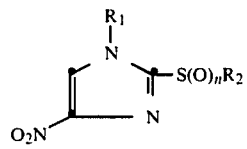

wherein $R_1$ is alkyl($C_1$–$C_6$) or phenyl substituted alkyl($C_7$–$C_9$);

$R_2$ is alkyl($C_1$–$C_{12}$) or phenyl; and n is 0, 1 or 2;

with the proviso that when n is 2, $R_1$ and $R_2$ are other than alkyl and a pharmaceutically acceptable carrier.

10. The composition of claim 9, wherein said $R_1$ alkyl is selected from the group consisting of methyl and propyl; said $R_2$ alkyl is selected from the group consisting of methyl, ethyl, propyl, octyl and decyl.

11. The composition of claim 10 wherein $R_1$ is methyl, $R_2$ is methyl, ethyl or propyl and n is 0 or 1.

12. The composition of claim 9, wherein the disease is trichomoniasis, amoebiasis, trypanosomiasis, enterohepatitis or PPLO.

13. The composition of claim 12 in oral form wherein the active ingredient is present at from 50 to 500 mg.

14. A method for the treatment of protozoal diseases is animals which comprises administering a non-mutagenic and antiprotozoal composition comprising an effective amount of a compound of the formula:

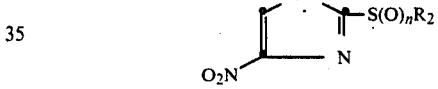

wherein $R_1$ is alkyl($C_1$–$C_6$) or phenyl substituted alkyl($C_7$–$C_9$);

$R_2$ is alkyl($C_1$–$C_{12}$) or phenyl; and n is 0, 1 or 2;

with the proviso that when n is 2, $R_1$ and $R_2$ are other than alkyl and an inert carrier.

15. The method of claim 12, wherein said $R_1$ alkyl is selected from the group consisting of methyl and propyl; said $R_2$ alkyl is selected from the group consisting of methyl, ethyl, propyl, octyl and decyl.

16. The method of claim 14, wherein the disease being treated is trichomoniasis, amoebiasis, trypanosomiasis, enterohepatitis or PPLO and the compound is administered in doses of from 25 to 1000 mg per day.

* * * * *